United States Patent [19]

Horiuchi et al.

[11] Patent Number: 5,710,335
[45] Date of Patent: Jan. 20, 1998

[54] PROCESS FOR PREPARING 3-(N,N-DISUBSTITUTED AMINO)PHENOL

[75] Inventors: Kenichiro Horiuchi; Bunji Sawano, both of Osaka-fu; Nobuaki Sasaki, Kyoto-fu; Mansuke Matsumoto, Hyogo-ken, all of Japan

[73] Assignees: Mitsui Toatsu Chemicals, Inc., Tokyo; Yamamoto Chemicals, Inc., Yao, both of Japan

[21] Appl. No.: 725,505

[22] Filed: Oct. 4, 1996

[30] Foreign Application Priority Data

Oct. 16, 1995 [JP] Japan ................. 7-267283

[51] Int. Cl.$^6$ ............................... C07C 209/18
[52] U.S. Cl. ............................... 564/403
[58] Field of Search ............................... 564/403, 439, 564/404, 408

[56] References Cited

U.S. PATENT DOCUMENTS

| | | | |
|---|---|---|---|
| 4,585,896 | 4/1986 | Harada et al. | 564/403 |
| 5,113,018 | 5/1992 | Kurano et al. | 564/403 |

*Primary Examiner*—Brian M. Burn
*Attorney, Agent, or Firm*—Burns, Doane, Swecker, & Mathis

[57] ABSTRACT

A process for preparing a 3-(N,N-disubstituted amino) phenol is herein disclosed which comprises reacting resorcin with a primary amine represented by formula (2):

$$R^1NH_2 \qquad (2)$$

wherein $R^1$ is an alkyl group, a cycloalkyl group, an alkenyl group, an alkoxyalkyl group, an aryl group or an aralkyl group, terminating the reaction when the conversion of resorcin is 50 mol % or more and when the amount of an N,N'-disubstituted-m-phenylenediamine as a by-product is 2 mol % or less of the amount of used resorcin, adding an alkyl halide represented by formula (3):

$$R^2X \qquad (3)$$

wherein $R^2$ is an alkyl group or a cycloalkyl group; and X is a halogen atom, to the obtained reaction mixture, adding an aqueous alkaline solution to the resultant reaction mixture to dissolve unreacted resorcin in the aqueous phase, extracting the 3-(N,N-disubstituted amino)phenol with an organic solvent, and then recovering unreacted resorcin from the aqueous phase. According to this process, the high-purity 3-(N,N-disubstituted amino)phenol can be prepared from resorcin in a substantially high yield, the production of by-products being inhibited.

5 Claims, No Drawings

PROCESS FOR PREPARING 3-(N,N-DISUBSTITUTED AMINO)PHENOL

BACKGROUND OF THE INVENTION

1. Field of the Invention

The present invention relates to a process for preparing 3-(N,N-disubstituted amino)phenols useful as organic industrial chemicals, various dyestuff intermediates and the like.

2. Description of the Related Art

With regard to preparation methods of 3-(N,N-disubstituted amino)phenols, many suggestions have heretofore been made. For example, Japanese Patent Laid-open Nos. 140053/1993 (U.S. Pat. No. 5,245,081), 186407/1993 and 271515/1994 (U.S. Pat. No. 5,442,121) disclose a method which comprises reacting resorcin as a starting material with a primary amine to obtain a 3-(N-monosubstituted amino)phenol, and successively reacting the same with an alkylating agent to obtain a 3-(N,N-disubstituted)aminophenol.

In Japanese Patent Laid-open No. 140053/1993 (U.S. Pat. No. 5,245,081), it has been disclosed that, in order to obtain 3-(N-monosubstituted amino)phenol which is an intermediate product, resorcin is reacted with a primary amine at a temperature of 180° to 250° C. under a pressure of 3 to 40 bars in the presence of phosphorous acid or a phosphorous acid ester or a mixture thereof. In this case, most of resorcin which has not been converted into the 3-(N-monosubstituted amino)phenol is changed into by-products, and in consequence, it can not be recovered.

In Japanese Patent Application Laid-open No. 186407/1993, resorcin is reacted with an alkylamine, and without isolating 3-(N-monoalkylamino)phenol from a reaction solution, an alkylating agent is then added to the reaction solution to obtain a 3-(N,N-dialkylamino)phenol. However, when resorcin is reacted with the alkylamine under reaction conditions described in examples of the disclosed patent, resorcin which has not been converted into the 3-(N-monoalkylamino)phenol is changed into by-products, as described above, or even in the case that resorcin remains, this resorcin is contaminated with a large amount of the by-products. Therefore, the purity of the recovered resorcin is too low for its reuse.

Japanese Patent Application Laid-open No. 271515/1994 (U.S. Pat. No. 5,442,121) has disclosed a method for obtaining an N,N-disubstituted aminophenol. First of all, a dihydric phenol is reacted with a primary amine, and a primary amine salt of the dihydric phenol which is inevitably present in a reaction mixture is thermally decomposed. Next, at least the primary amine is removed from the reaction mixture, and an N-substituted aminophenol is then separated from the reaction mixture by distillation. Afterward, the thus obtained N-substituted aminophenol is reacted with an alkylaldehyde in the presence of a reducing catalyst in an organic solvent in a hydrogenous atmosphere to carry out reductive alkylation. In this method, the primary amine and the primary amine salt of the dihydric phenol, which poison the catalyst for the reductive alkylation reaction and which deteriorate its catalytic activity, are required to be removed form the system after the reaction of the dihydric phenol with the primary amine, and therefore, it is necessary to decompose the primary amine salt of the dihydric phenol into the dihydric phenol and then to distill the dihydric phenol. However, since the boiling point of the dihydric phenol is close to that of the N-substituted aminophenol, it is extremely difficult to separate the two compounds from each other by the distillation. Moreover, some high-boiling by-products can be removed by the distillation, but N,N-disubstituted-m-phenylenediamine and N-substituted-3,3'-dihydroxydiphenylamine which are the main by-products cannot be removed. For this reason, even if the dihydric phenol (resorcin or the like) is recovered, it contains the impurities, whereby the usable dihydric phenol cannot be obtained.

The above-mentioned three methods can each obtain the acceptable results in point of the yield of the 3-(N,N-disubstituted amino)phenol, but these methods are unsuitable for the application to industrial production, because in these conventional methods, the higher a resorcin conversion is, the larger the production of the by-products is, and the purity of recovered resorcin is low and so its reusability is also poor.

SUMMARY OF THE INVENTION

An object of the present invention is to provide a process for preparing a high-purity 3-(N,N-disubstituted amino) phenol in a substantially high yield which can solve the problems of conventional methods, can restrain the production of by-products, and can recover the almost all amount of unreacted resorcin in a high purity.

The present inventors have intensively investigated in order to achieve the above-mentioned object. As a result, the present invention has been completed.

That is to say, the present invention is directed to a preparation process of a 3-(N,N-disubstituted amino)phenol represented by formula (1):

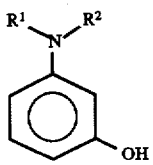

(1)

wherein $R^1$ is an alkyl group, a cycloalkyl group, an alkenyl group, an alkoxyalkyl group, an aryl group or an aralkyl group; and $R^2$ is an alkyl group or a cycloalkyl group, which comprises the following steps (a) to (d):

(a) the step of reacting resorcin with a primary amine represented by formula (2):

(2)

wherein $R^x$ is the same as defined above, and then terminating the reaction when the conversion of resorcin is 50 mol % or more and when the amount of an N,N'-disubstituted-m-phenylenediamine as a by-product is 2 mol % or less of the amount of used resorcin, thereby obtaining a reaction mixture including a 3-(N-monosubstituted amino)phenol, (b) the step of adding an alkyl halide represented by formula (3):

(3)

wherein $R^2$ is the same as defined above; and X is a halogen atom, to the reaction mixture obtained in step (a) to obtain a reaction mixture including the 3-(N,N-disubstituted amino) phenol, (c) the step of adding an aqueous alkaline solution to the reaction mixture obtained in step (b) to dissolve unreacted resorcin in the aqueous alkaline solution, and extracting the 3-(N,N-disubstituted amino)phenol with an organic solvent, and (d) the step of recovering unreacted resorcin from the aqueous alkaline solution layer of step (c).

According to the process of the present invention, the production of by-products is very small, and since resorcin recovered from a reaction system has a high purity, its reuse is possible, and the high-purity 3-(N,N-disubstituted amino) phenol can be prepared in a substantially high yield.

DETAILED DESCRIPTION OF THE PREFERRED EMBODIMENTS

In a primary amine represented by in the above-mentioned formula (2), $R^1$ is an alkyl group, a cycloalkyl group, an alkenyl group, an alkoxyalkyl group, an aryl group or an aralkyl group, and more preferably, $R^1$ is a branched or a straight-chain alkyl group having 1 to 10 carbon atoms, a cycloalkyl group having 5 to 10 carbon atoms, an alkenyl group having 2 to 10 carbon atoms, an alkoxyalkyl group having 2 to 10 carbon atoms, an aryl group having 6 to 10 carbon atoms or an aralkyl group having 7 to 10 carbon atoms.

Particularly, $R^1$ is preferably a branched or a straight-chain alkyl group having 1 to 8 carbon atoms or a cycloalkyl group of 5 to 8 carbon atoms.

Typical examples of the primary amine represented by formula (2) include N-branched or straight-chain alkylamine such as methylamine, ethylamine, n-propylamine, isopropylamine, n-butylamine, isobutylamine, sec-butylamine, tertbutylamine, n-pentylamine, isopentylamine, 2,2-dimethylpropylamine, 1-ethylpropylamine, n-hexylamine, 1-methylpentylamine, n-heptylamine, 2-methylhexylamine, 1-ethylpentylamine, 2-ethylhexylamine, n-nonylamine and n-decylamine, N-cycloalkylamines such as cyclopentylamine, cyclohexylamine, (4'-methylcyclohexyl)amine, cycloheptylamine, cyclooctylamine and cyclodecylamine, N-alkenylamines such as allylamine, β-butenylamine and β-n-pentenylamine, N-alkoxyalkyl amines such as 2-methoxyethylamine, 2-ethoxyethylamine, 2-n-propoxyethylamine, 2-isopropoxyethylamine, 2-n-butoxyethylamine, 2-n-pentyloxyethylamine, 2-n-hexyloxyethylamine, 2-n-octyloxyethylamine, 3-methoxypropylamine, 3-ethoxypropylamine, 3-n-propoxypropylamine, 3-isopropoxypropylamine, 3-n-butoxypropylamine, 3-isobutoxypropylamine, 3-n-pentyloxypropylamine, 3-n-hexyloxypropylamine, 4-methoxybutylamine, 5-ethoxypentylamine and tetrahydrofurfurylamine, N-arylamines such as aniline, 3-methylaniline, 4-methylaniline, 4-ethylaniline and 4-methoxyaniline, and N-aralkylamines such as benzylamine, 2-phenylethylamine, 3-phenylpropylamine and 4-phenylbutylamine. The more preferable primary amines are compounds represented by formula (2) in which $R^1$ is an alkyl group or a cycloalkyl group, and particularly preferable are an N-branched or a straight-chain alkylamine having 1 to 8 carbon atoms and an N-cycloalkylamine having 5 to 8 carbon atoms.

In an alkyl halide compound represented by the above-mentioned formula (3), $R^2$ is an alkyl group or a cycloalkyl group, and preferably it is an alkyl group of 1 to 10 carbon atoms or a cycloalkyl group of 5 to 10 carbon atoms. More preferably, it is an alkyl group of 1 to 8 carbon atoms.

In the alkyl halide compound represented by formula (3), X is a halogen atom, and it is preferably a halogen atom such as a chlorine atom, a bromine atom or an iodine atom. Above all, the bromine atom is preferable.

Typical examples of the alkyl halide compound represented by formula (3) include methyl bromide, methyl iodide, ethyl bromide, ethyl iodide, n-propyl chloride, n-propyl bromide, n-propyl iodide, isopropyl chloride, isopropyl bromide, isobutyl chloride, isobutyl bromide, sec-butyl bromide, tert-butyl bromide, tert-butyl chloride, n-pentyl bromide, isopentyl bromide, neopentyl bromide, 1-ethylpropyl bromide, n-hexyl bromide, 1-methylpentyl bromide, n-heptyl bromide, 2-methylhexyl bromide, 2-ethylhexyl bromide, n-nonyl bromide, n-decyl bromide, cyclopentyl bromide, cyclohexyl chloride, cyclohexyl bromide, 4'-methylcyclohexyl bromide, cycloheptyl bromide, cyclooctyl bromide, cyclodecyl bromide, cyclohexylmethyl bromide and cyclohexylethyl bromide.

In the preparation process of the 3-(N,N-disubstituted amino)phenol represented by the above-mentioned formula (1) of the present invention, resorcin is first reacted with the primary amine represented by formula (2) in step (a) to obtain a reaction mixture including a 3-(N-monosubstituted amino)phenol. The main by-products in this reaction include an N,N'-disubstituted-m-phenylenediamine and a 3,3'-dihydroxy-N-substituted diphenylamine, and other various by-products are also produced therein. Most of these by-products get into the final end product or react with the alkyl halide in the next step (b), and therefore it is preferable that they are removed. However, it is difficult to remove the by-products without any loss of the desired 3-(N-monosubstituted amino)phenol. In this step, it is impossible to control the production of the by-products, and in the case of the conventional techniques presently used, a production rate of the by-products increases, as a production ratio of the 3-(N-monosubstituted amino) phenol rises.

The present inventors have found that when a conversion of resorcin is within a specific range, the production of the by-products is very small. Resorcin present after the completion of step (a) does not react with the alkyl halide in step (b) under the conditions of the present invention, and since substantial all of the above-mentioned unreacted resorcin can be recovered in step (d), the loss of resorcin hardly takes place.

In order to maintain the production ratio of the by-products at a low level, it is necessary to restrain the conversion of resorcin at a low level, as described above. However, when the conversion of resorcin is fairly low, a production efficiency is low, which is disadvantageous from the viewpoint of a manufacturing cost. Accordingly, the conversion of resorcin is preferably 50% or more, more preferably 65% or more.

Moreover, as described above, the higher the conversion of resorcin is, the larger the production of the by-products is. For this reason, the upper limit of the conversion of resorcin needs to be regulated to a certain value or less, but a relation between the conversion of resorcin and the production of the by-products depends somewhat on various conditions in step (a) such as presence/absence and a kind of catalyst, a reaction pressure and a reaction temperature. In order to grasp the upper limit of the optimum conversion, the present inventors have found that the production of the N,N'-disubstituted-m-phenylenediamine which is the main by-product can be utilized as a convenient index. That is to say, if the production of the N,N'-disubstituted-m-phenylenediamine is 2 mol % or less of amount of used resorcin, the production of the other by-products in step (a) is also low, so that the purity of the finally obtainable 3-(N,N-disubstituted amino)phenol can heighten. Furthermore, in step (c), the amount of the by-products which dissolves in the aqueous alkaline solution is also fairly small, which enables resorcin recovered in step (d) to be used as a raw material of the next reaction without further purification. In consequence, the substantial yield of the 3-(N,N-disubstituted amino)phenol from resorcin is substantially 100%.

As described above, the relation between the conversion of resorcin and the amount of the by-products depends slightly on the conditions of step (a) sometimes, but if the conditions are denoted only by the conversion of resorcin, it is important that the conversion of resorcin is preferably in the range of 50 to 85%, more preferably 65 to 80%.

In step (a), a molar ratio of the used primary amine to resorcin is preferably in the range of 0.8 to 1.4, more preferably 0.9 to 1.2. The reaction can be carried out even in a catalyst-free condition or in the presence of the catalyst, and it can also be done in a suitable organic solvent and under an increased pressure. The reaction conditions depends somewhat on the presence/absence of the catalyst and the solvent, but the conditions described in step (a) can be established by, for example, employing atmospheric pressure, a reaction temperature of 100° to 160° C. and a reaction time of 2 to 24 hours. In the case that the increased pressure is used, the reaction time can be shortened. An optimum reaction end point can be presumed or decided by, for example, sampling a reaction mixture at suitable intervals of time, analyzing the samples by the use of gas chromatography or liquid chromatography to draw a production curve of N,N'-disubstituted-m-phenylenediamine and/or 3-(N-monosubstituted amino)phenol, and then utilizing this production curve.

In order to terminate the reaction of resorcin with the primary amine in the above-mentioned step (a), for example, the reaction system may be cooled to 50° C. or less.

Examples of the usable catalyst include halides of metals such as copper, cobalt, zinc, nickel, magnesium, tin, antimony, vanadium and iron, halogenated ammonium salts of metals such as copper, cobalt and nickel, oxides of metals such as gallium, silicon, zinc, molybdenum, tungsten, antimony, vanadium, iron and aluminum, phosphates of metals such as zinc and nickel, organic carboxylic acids such as acetic acid, propionic acid, caproic acid, palmitic acid, stearic acid, succinic acid, malonic acid, adipic acid, glutaric acid, benzoic acid, phenylacetic acid, naphthoic acid and phthalic acid, phosphoric acid and polyphosphoric acid.

No particular restriction is put on the amount of the catalyst to be used, any amount of the same can be employed, so long as it permits the exertion of a desired reaction promotion effect. In general, the catalyst is used in an amount of about 1 to 30 mol % with respect to the amount of resorcin.

The usable organic solvent preferably is excellent in solubility of the 3-(N-monosubstituted amino)phenol and poor in solubility in water.

Typical examples of the organic solvent include aromatic hydrocarbon solvents such as benzene, toluene, o-xylene, m-xylene, p-xylene, ethylbenzene, p-diethylbenzene, 1,2,4-trimethylbenzene, 1,3,5-trimethylbenzene, tetralin and α-methylnaphthalene, aliphatic hydrocarbon solvents such as pentane, hexane, heptane, octane, decane, cyclohexane and decalin, aliphatic halogenated hydrocarbon solvents such as dichloromethane, chloroform, tetrachloromethane, tetrachloroethylene, 1,2-dichloroethane, 1,1,1-trichloroethane, 1,1,2-trichloroethane and 1,1,2,2-tetrachloroethane, ether solvents such as diisopropyl ether, di-n-butyl ether, anisole and diphenyl ether, ester solvents such as ethyl acetate, butyl acetate and amyl acetate, and alcoholic solvents such as n-hexanol, n-heptanol, n-octanol, 2-ethylhexanol, n-decanol and cyclohexanol.

These solvents may be used singly or in a combination of two or more thereof. Of these solvents, the hydrocarbon solvents are preferable, the aromatic hydrocarbon solvents and the aliphatic hydrocarbon solvents are more preferable, and the aromatic hydrocarbon solvents are most preferable.

No particular restriction is put on the amount of the organic solvent to be used, but in general, it is 10% by weight or more of the weight of resorcin. However, if the organic solvent is used in an excessive amount, a manufacture efficiency deteriorates. Therefore, it is preferably in the range of 10 to 10000% by weight, more preferably 20 to 5000% by weight of the weight of resorcin.

After the termination of the reaction in step (a), it is preferable to recover and remove the unreacted primary amine, because a manufacturing cost can be reduced or the possibility of secondary reactions in subsequent steps can be avoided.

Moreover, when the organic solvent is used in the reaction of step (a), it is preferable to recover and remove the used organic solvent after the termination of the reaction, because secondary reactions in step (b) can be inhibited.

In step (b), the alkyl halide represented by formula (3) is added to the reaction mixture obtained in the above-mentioned step (a) to obtain a reaction mixture including the 3-(N,N-disubstituted amino)phenol. In this step, it is preferable that neither an alkali nor a solvent is used. If the alkali or the solvent is used, a secondary reaction such as ortho-alkylation takes place, so that the purity and yield of the desired 3-(N,N-disubstituted amino)phenol deteriorate sometimes. However, when the viscosity of the reaction system is so high that a stirring efficiency is low, the hydrocarbon solvent may be used.

In step (b), a molar ratio of the alkyl halide to be used is preferably in the range of 0.8 to 1.5, more preferably 0.9 to 1.2 with respect to resorcin.

The reaction temperature in step (b) is preferably in the range of 50° to 150° C. The reaction time depends on the reaction temperature, but it is in the range of 2 to 40 hours.

After the completion of step (b), it is preferable that the remaining alkyl halide is removed, because for example, the production of by-products such as 3-alkoxy-N,N-disubstituted aniline can be inhibited.

In step (c), an aqueous alkaline solution is added to the reaction mixture in which the alkylation has been completed, whereby unreacted resorcin is dissolved therein. On the other hand, the 3-(N,N-disubstituted amino)phenol is extracted with the organic solvent which is separable from an aqueous layer. As the organic solvent which is separable from the aqueous layer, any of the reaction solvents enumerated in step (a) can be used. Almost all of resorcin is dissolved in the aqueous alkaline solution, so that it does not substantially get into an organic layer.

Examples of a usable alkali for the aqueous alkaline solution include alkali metal compounds such as lithium hydroxide, potassium hydroxide, sodium hydroxide, potassium carbonate, sodium carbonate, potassium hydrogencarbonate and sodium hydrogencarbonate, and alkaline earth metal compounds such as calcium hydroxide, magnesium hydroxide and calcium carbonate. Above all, sodium hydroxide and potassium hydroxide are particularly preferable.

The amount of the alkali is preferably in the range of 1.0 to 2.5 moles per mol of resorcin used in step (a), and the amount of water is preferably 2 to 20 times, more preferably 5 to 8 times as much as the weight of resorcin used in step (a).

In step (d), as a technique for recovering resorcin from the aqueous alkaline solution obtained in step (c), there can be used a method which comprises neutralizing the aqueous alkaline solution, and then distilling off water to recover resorcin, or another method which comprises neutralizing or acidifying the aqueous alkaline solution, and then extracting resorcin with a polar solvent which is separable from the aqueous layer.

When the aqueous alkaline solution obtained in step (c) is neutralized or acidified, a mineral acid such as hydrochloric acid, sulfuric acid or nitric acid can suitably be used.

As the polar solvent which is separable from the aqueous layer, an alkyl ketone can suitably used, and typical examples of the alkyl ketone include methyl propyl ketone, methyl isobutyl ketone (MIBK), diethyl ketone, diisopropyl ketone, ethyl isobutyl ketone, propyl butyl ketone and diisobutyl ketone. In addition, an ether such as diethyl ether can also be used.

In the preparation process of the present invention, the respective steps can be carried out in the atmosphere, but in order to prevent the coloring of the obtained 3-(N,N-disubstituted amino)phenol, they are preferably done under the atmosphere of an inert gas such as nitrogen, argon or helium.

Next, the present invention is described in more detail with reference to examples, but the scope of the present invention should not be limited to these examples at all.

EXAMPLE 1

Step (a)

Under a nitrogen atmosphere, 110 g (1 mol) of resorcin was heated up to 140° C. to melt it, and while a temperature of 140° to 145° C. was maintained, 87.6 g (1.2 mol) of n-butylamine were added dropwise thereto over 10 hours. After the completion of the dropping, reaction was further carried out at the same temperature for 6 hours. After the solution was cooled to room temperature to terminate the reaction, 31.8 g of unreacted n-butylamine were recovered by distillation, thereby obtaining a reaction mixture. This reaction mixture was analyzed by a high-performance liquid chromatography. As a result, it was apparent that in the reaction mixture, there were included 123.8 g of 3-(N-n-butylamino)phenol (yield based on resorcin: 75 mol %), 26.4 g of resorcin (conversion of resorcin: 76 mol %), and 0.66 g of N N'-di-n-butyl-m-phenylenediamine (production ratio based on resorcin: 0.3 mol %).

If it was assumed that all peaks other than the above-mentioned peaks observed on a liquid chromatogram were attributable to by-products other than N,N'-di-n-butyl-m-phenylenediamine, the amount of the other by-products was 0.8% by weight.

Step (b)

137 g (1 mol) of n-butyl bromide were added to the reaction mixture obtained in step (a), and reaction was then carried out at 80° to 90° C. for 8 hours. After the reaction, 32.4 g of unreacted n-butyl bromide were recovered by distillation to obtain a reaction mixture. This reaction mixture was analyzed by a high-performance liquid chromatography, and as a result, in the reaction mixture, there was included 165.8 g of 3-(N,N-di-n-butylamino)phenol [yield based on 3-(N-n-butylamino)phenol: 100 mol %].

Step (c)

200 g of a 25% aqueous sodium hydroxide solution were, added to the reaction mixture obtained in step (b) to alkalify it, and 3-(N,N-di-n-butylamino)phenol was extracted with 300 ml of toluene.

The resulting toluene extract was analyzed by a high-performance liquid chromatography, and as a result, it was apparent that the total amount of 3-(N,N-di-n-butylamino)phenol produced in step (b) was included in this toluene extract, and its purity was 99.4% by weight. Resorcin was not included in this toluene extract.

Step (d)

The aqueous sodium hydroxide solution obtained in step (c) was neutralized with dilute hydrochloric acid, and water was then distilled off. Afterward, extraction operation was repeated 3 times with 200 ml of diethyl ether, and diethyl ether was then distilled off, thereby recovering 26.4 g of unreacted resorcin.

EXAMPLE 2

Step (a)

Under a nitrogen atmosphere, 26.1 g (0.3 mol) of isopentylamine were added to 110 g (1 mol) of resorcin, and the mixture was then stirred at 145° to 150° C. for 4 hours. Afterward, while the same temperature was maintained, 69.6 g (0.8 mol) of isopentylamine were added dropwise thereto over 7 hours. After the completion of the dropping, reaction was carried out at the same temperature for 4 hours. After the solution was cooled to room temperature to terminate the reaction, 30.7 g of unreacted isopentylamine were recovered by distillation, thereby obtaining a reaction mixture. This reaction mixture was analyzed by a high-performance liquid chromatography. As a result, it was apparent that in the reaction mixture, there were included 130.7 g of 3-(N-n-isopentylamino)phenol (yield based on resorcin: 73 mol %), 27.8 g of resorcin (conversion of resorcin: 75 mol %), and 1.24 g of N,N'-di-n-isopentyl-m-phenylenediamine (production ratio based on resorcin: 0.5 mol %).

If it was assumed that all peaks other than the above-mentioned peaks observed on a liquid chromatogram were attributable to by-products other than N,N'-di-n-isopentyl-m-phenylenediamine, the amount of the other by-products was 1.2% by weight.

Step (b)

156 g (1 mol) of ethyl iodide were added to the reaction mixture obtained in step (a), and reaction was then carried out at 70° to 75° C. for 10 hours. After the reaction, 38.6 g of unreacted ethyl iodide were recovered by distillation to obtain a reaction mixture. This reaction mixture was analyzed by a high-performance liquid chromatography, and as a result, in the reaction mixture, there was included 151.1 g of 3-(N-ethyl-N-isopentylamino)phenol (yield based on 3-N-isopentylaminophenol: 100 mol %).

Step (c)

200 g of a 25% aqueous sodium hydroxide solution were added to the reaction mixture obtained in step (b) to alkalify it, and 3-(N-ethyl-N-isopentylamino)phenol was extracted with 300 ml of chlorobenzene.

The resulting chlorobenzene extract was analyzed by a high-performance liquid chromatography, and as a result, it was apparent that the total amount of 3-(N-ethyl-N-isopentylamino)phenol produced in step (b) was included in this chlorobenzene extract, and its purity was 99.0% by weight. Resorcin was not included in this toluene extract.

Step (d)

55 ml of 35% hydrochloric acid was added to the aqueous sodium hydroxide solution obtained in step (c) to acidify it. Afterward, extraction operation was repeated 3 times with 200 ml of methyl isobutyl ketone, and methyl isobutyl ketone was then distill off, thereby recovering 27.8 g of unreacted resorcin.

EXAMPLE 3

Step (a)

Under a nitrogen atmosphere, 49.5 g (0.5 mol) of cyclohexylamine were added to 110 g (1 mol) of resorcin, and the mixture was then stirred at 145° to 150° C. for 5 hours. Afterward, while the same temperature was maintained, 59.4 g (0.6 mol) of cyclohexylamine was added dropwise thereto over 6 hours. After the completion of the dropping, reaction was carried out at the same temperature for 4 hours. After the solution was cooled to room temperature to terminate the reaction, 39.6 g of unreacted cyclohexylamine were recovered by distillation, thereby obtaining a reaction mixture. This reaction mixture was analyzed by a high-performance liquid chromatography. As a result, it was apparent that in the reaction mixture, there were included 131.8 g of 3-(N-cyclohexylamino)phenol (yield based on resorcin: 69 mol %), 32.6 g of resorcin (conversion of resorcin: 70 mol %), and 1.09 g of N,N'-dicyclohexyl-m-phenylenediamine (production ratio based on resorcin: 0.4 mol %).

If it was assumed that all peaks other than the above-mentioned peaks observed on a liquid chromatogram were attributable to by-products other than N,N'-dicyclohexyl-m-phenylenediamine, the amount of the other by-products was 1.3% by weight.

Step (b)

142 g (1 mol) of methyl iodide were added to the reaction mixture obtained in step (a), and reaction was then carried out at 45° to 50° C. for 10 hours. After the reaction, 41.1 g of unreacted methyl iodide were recovered by distillation to obtain a reaction mixture. This reaction mixture was analyzed by a high-performance liquid chromatography, and as a result, in the reaction mixture, there was included 141.5 g of 3-(N-cyclohexyl-N-methylamino)phenol [yield based on 3-(N-cyclohexylamino)phenol: 100 mol %].

Step (c)

200 g of a 25% aqueous sodium hydroxide solution were added to the reaction mixture obtained in step (b) to alkalify it, and 3-(N-cyclohexyl-N-methylamino)phenol was extracted with 300 ml of toluene.

The resulting toluene extract was analyzed by a high-performance liquid chromatography, and as a result, it was apparent that the total amount of 3-(N-cyclohexyl-N-methylamino)phenol produced in step (b) was included in this toluene extract, and its purity was 99.2% by weight. Resorcin was not included in this toluene extract.

Step (d)

60 ml of 35% hydrochloric acid was added to the aqueous sodium hydroxide solution obtained in step (c) to acidify it. Afterward, extraction operation was repeated 3 times with 200 ml of methyl isobutyl ketone, and methyl isobutyl ketone was then distill off, thereby recovering 32.6 g of unreacted resorcin.

EXAMPLE 4

Step (a)

Under a nitrogen atmosphere, 87.0 g (1 mol) of n-pentylamine were added to 110 g (1 mol) of resorcin, and reaction was then carried out at 140° to 145° C. for 20 hours. After the reaction mixture was cooled to room temperature to terminate the reaction, 13.9 g of unreacted n-pentylamine were recovered by distillation, thereby obtaining a reaction mixture. This reaction mixture was analyzed by a high-performance liquid chromatography. As a result, it was apparent that in the reaction mixture, there were included 139.6 g of 3-(N-n-pentylamino)phenol (yield based on resorcin: 78 mol %), 17.6 g of resorcin (conversion of resorcin: 84 mol %), and 4.22 g of N,N'-di-n-pentyl-m-phenylenediamine (production ratio based on resorcin: 1.7 mol %).

If it was assumed that all peaks other than the above-mentioned peaks observed on a liquid chromatogram were attributable to by-products other than N,N'-di-n-pentyl-m-phenylenediamine, the amount of the other by-products was 3.9% by weight.

Step (b)

151 g (1 mol) of n-pentyl bromide were added to the reaction mixture obtained in step (a), and reaction was then carried out at 125° to 130° C. for 6 hours. After the reaction, 31.8 g of unreacted n-pentyl bromide were recovered by distillation to obtain a reaction mixture. This reaction mixture was analyzed by a high-performance liquid chromatography, and as a result, in the reaction mixture, there was included 194.2 g of 3-(N,N-di-n-pentylamino)phenol [yield based on 3-(N-n-pentylamino)phenol: 100 mol %].

Step (c)

200 g of a 25% aqueous sodium hydroxide solution were added to the reaction mixture obtained in step (b) to alkalify it, and 3-(N,N-di-n-pentylamino)phenol was extracted with 300 ml of toluene.

The resulting toluene extract was analyzed by a high-performance liquid chromatography, and as a result, it was apparent that the total amount of 3-(N,N-di-n-pentylamino)phenol produced in step (b) was included in this toluene extract, and its purity was 98.3% by weight. Resorcin was not included in this toluene extract.

Step (d)

60 ml of 35% hydrochloric acid was added to the aqueous sodium hydroxide solution obtained in step (c) to acidify it. Afterward, extraction operation was repeated 3 times with 200 ml of methyl isobutyl ketone, and methyl isobutyl ketone was then distill off, thereby recovering 17.5 g of unreacted resorcin.

EXAMPLE 5

Step (a)

Under a nitrogen atmosphere, 5.7 g of unused resorcin were added to 104.3 g of resorcin recovered in Examples 1 to 4 so that its total volume might be 110 g (1 mol), and the mixture was then heated up to 140° C. to melt it. While a temperature of 145° to 150° C. was maintained, 87.6 g (1.2 mol) of n-butylamine were added dropwise thereto over 8 hours. After the completion of the dropping, reaction was further carried out at the same temperature for 5 hours. After the solution was cooled to room temperature to terminate the reaction, 30.5 g of unreacted n-butylamine were recovered by distillation, thereby obtaining a reaction mixture. This reaction mixture was analyzed by a high-performance liquid chromatography. As a result, it was apparent that in the reaction mixture, there were included 125.4 g of 3-(N-n-butylamino)phenol (yield based on resorcin: 76 mol %), 25.8 g of resorcin (conversion of resorcin: 77 mol %), and 0.74 g of N,N'-di-n-butyl-m-phenylenediamine (production ratio based on resorcin: 0.3 mol %).

If it was assumed that all peaks other than the above-mentioned peaks observed on a liquid chromatogram were attributable to by-products other than N,N'-di-n-butyl-m-phenylenediamine, the amount of the other by-products was 0.9% by weight.

Step (b)

137 g (1 mol) of n-butyl bromide were added to the reaction mixture obtained in step (a), and reaction was then carried out at 80° to 90° C. for 8 hours. After the reaction, 31.5 g of unreacted n-butyl bromide was recovered by distillation to obtain a reaction mixture. This reaction mixture was analyzed by a high-performance liquid chromatography, and as a result, in the reaction mixture, there was included 168.0 g of 3-(N,N-di-n-butylamino)phenol [yield based on 3-(N-n-butylamino)phenol: 100 mol %].

Step (c)

200 g of a 25% aqueous sodium hydroxide solution were added to the reaction mixture obtained in step (b) to alkalify it, and 3-(N,N-di-n-butylamino)phenol was extracted with 300 ml of toluene.

The resulting toluene extract was analyzed by a high-performance liquid chromatography, and as a result, it was apparent that the total amount of 3-(N,N-di-n-butylamino) phenol produced in step (b) was included in this toluene extract, and its purity was 99.1% by weight. Resorcin was not included in this toluene extract.

Step (d)

The aqueous sodium hydroxide solution obtained in step (c) was neutralized with dilute hydrochloric aid, and water was then distilled off. Afterward, extraction operation was repeated 3 times with 200 ml of methyl isobutyl ketone, and methyl isobutyl ketone was then distilled off, thereby recovering 25.3 g of unreacted resorcin.

COMPARATIVE EXAMPLE 1

Step (a')

Under a nitrogen atmosphere, 21.9 g (0.3 mol) of n-butylamine were added to 110 g (1 mol) of resorcin, and the mixture was then stirred at 175° to 180° C. for 2 hours. At the same temperature, 65.7 g (0.9 mol) of n-butylamine were then added dropwise to this mixture over 2 hours. After the completion of the dropping, reaction was carried out at the same temperature for 6 hours. After the solution was cooled to room temperature to terminate the reaction, 11.8 g of unreacted n-butylamine were recovered by distillation, thereby obtaining a reaction mixture. This reaction mixture was analyzed by a high-performance liquid chromatography. As a result, it was apparent that in the reaction mixture, there were included 107.3 g of 3-(N-n-butylamino)phenol (yield based on resorcin: 65 mol %), 5.5 g of resorcin (conversion of resorcin: 95 mol %), and 19.8 g of N,N'-di-n-butyl-m-phenylenediamine (production ratio based on resorcin: 9.0 mol %).

If it was assumed that all peaks other than the above-mentioned peaks observed on a liquid chromatogram were attributable to by-products other than N,N'-di-n-butyl-m-phenylenediamine, the amount of the other by-products was 20.5% by weight.

Step (b)

137 g (1 mol) of n-butyl bromide were added to the reaction mixture obtained in step (a'), and reaction was then carried out at 80° to 90° C. for 8 hours. After the reaction, the recovery of unreacted n-butyl bromide was tried by distillation, but it could not be accomplished. This reaction mixture was analyzed by a high-performance liquid chromatography, and as a result, in the reaction mixture, there were included 143.6 g of 3-(N,N-di-n-butylamino)phenol [yield based on 3-(N-n-butylamino)phenol: 100 mol %], and 29.8 g of N,N,N',N'-tetra-n-butyl-m-phenylenediamine In addition, peaks of by-products having unidentified structures were also observed.

Step (c)

200 g of a 25% aqueous sodium hydroxide solution were added to the reaction mixture obtained in step (b) to alkalify it, and 3-(N,N-di-n-butylamino)phenol was extracted with 300 ml of toluene.

The resulting toluene extract was analyzed by a high-performance liquid chromatography, and as a result, it was apparent that the total amount of 3-(N,N-di-n-butylamino) phenol produced in step (b) was included in this toluene extract, and its purity was 82.8% by weight. Resorcin was not included in this toluene extract.

Step (d)

30 ml of 35% hydrochloric acid was added to the aqueous sodium hydroxide solution obtained in step (c) to acidify it. Afterward, extraction operation was repeated twice with 200 ml of methyl isobutyl ketone, and methyl isobutyl ketone was then distill off, thereby obtaining 41.6 g of high-boiling by-products containing 5.5 g of unreacted resorcin. From the resulting residue, high-purity resorcin could not be recovered.

COMPARATIVE EXAMPLE 2

Step (a")

The same procedure as in Comparative Example 1 was repeated except that reaction temperature in a step (a') of Comparative Example 1 was in the range of 165° to 170° C. The resulting reaction mixture was analyzed by a high-performance liquid chromatography. As a result, it was apparent that in the reaction mixture, there were included 123.8 g of 3-(N-n-butylamino)phenol (yield based on resorcin: 82%), 11.0 g of resorcin (conversion of resorcin: 90 mol %), and 5.5 g of N,N'-di-n-butyl-m-phenylenediamine (production ratio based on resorcin: 2.5 mol %).

If it was assumed that all peaks other than the above-mentioned peaks observed on a liquid chromatogram were attributable to the other by-products, the amount of the other by-products was 5.9% by weight.

Step (b)

The same procedure and analysis as in Comparative Example 1 were repeated, and as a result, in the resulting reaction mixture, there were included 181.2 g of 3-(N,N-di-n-butylamino)phenol [yield based on 3-(N-n-butylamino)phenol: 100 mol %], and 8.3 g of N,N,N',N'-tetra-n-butyl-m-phenylenediamine.

Step (c)

The same procedure and analysis as in Comparative Example 1 were repeated.

The total amount of 3-(N,N-di-n-butylamino)phenol produced in step (b) was included in a toluene extract, and its purity was 91.4% by weight. Resorcin was not included in this toluene extract.

Step (d)

The same procedure as in Comparative Example 1 was repeated, thereby obtaining 21.0 g of high-boiling by-products containing 11 g of unreacted resorcin. From these by-products, high-purity resorcin could not be recovered.

Summary of Results

Table 1 shows the conversion of resorcin, the yield of a 3-(N-monosubstituted amino)phenol and the ratio of formed by-products in each of steps (a), (a') and (a") as well as the purity of a desired product obtained in each of steps (c) of Examples 1 to 5 and Comparative Examples 1 and 2.

TABLE 1

|  | A | B | C | D | E |
|---|---|---|---|---|---|
| Example 1 | 76 mol % | 75 mol % | 0.3 mol % | 0.8 wt. % | 99.4 wt. % |
| Example 2 | 75 mol % | 73 mol % | 0.5 mol % | 1.2 wt. % | 99.0 wt. % |
| Example 3 | 70 mol % | 69 mol % | 0.4 mol % | 0.9 wt. % | 99.2 wt. % |
| Example 4 | 84 mol % | 78 mol % | 1.7 mol % | 3.9 wt. % | 98.3 wt. % |
| Example 5 | 77 mol % | 76 mol % | 0.3 mol % | 0.9 wt. % | 99.1 wt. % |
| Comp. Ex. 1 | 95 mol % | 65 mol % | 9.0 mol % | 20.5 wt. % | 82.8 wt. % |
| Comp. Ex. 2 | 90 mol % | 82 mol % | 2.5 mol % | 5.9 wt. % | 91.4 wt. % |

A: The conversion of resorcin in each of steps (a), step (a') of Comparative Example 1 and (a") of Comparative Example 2.

B: The yield (to resorcin) of the 3-(N-monosubstituted amino)phenol in each of steps (a), step (a') of Comparative Example 1 and (a") of Comparative Example 2.

C: The ratio of the N,N'-disubstituted-m-phenylenediamine formed in each of steps (a), step (a') of Comparative Example 1 and (a") of Comparative Example 2.

D: The ratio of by-products other than the N,N'-disubstituted-m-phenylenediamine formed in each of steps (a), step (a') of Comparative Example 1 and (a") of Comparative Example 2.

E: The purity of the 3-(N,N-disubstituted amino)phenol obtained in each of steps (c).

In Examples 1 to 5, the production of the by-products was very small, and the obtained 3-(N,N-disubstituted amino) phenols each had a very high purity.

Furthermore, as shown in Example 5, resorcin recovered in Examples 1 to 4 was usable as a raw material for a subsequent reaction, but in resorcin recovered in Comparative Example 1, a large amount of the by-products were included, and so its reuse was impossible.

As is apparent from the results described above, according to the process of the present invention, the production of the by-products is very small, and recovered resorcin has a high purity and so it is reusable. In addition, a high-purity 3-(N,N-disubstituted amino)phenol can be prepared in a substantially high yield.

What is claimed is:

1. A process for preparing a 3-(N,N-disubstituted amino) phenol represented by formula (1):

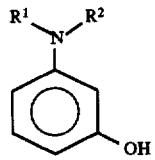

(1)

wherein $R^1$ is an alkyl group, a cycloalkyl group, an alkenyl group, an alkoxyalkyl group, an aryl group or an aralkyl group; and $R^2$ is an alkyl group or a cycloalkyl group, said process comprising the following steps (a) to (d):

(a) the step of reacting resorcin with a primary amine represented by formula (2):

$$R^1NH_2 \qquad (2)$$

wherein $R^1$ is the same as defined above, and then terminating the reaction when the conversion of resorcin is 50 mol % or more and when the amount of an N,N'-disubstituted-m-phenylenediamine as a by-product is 2 mol % or less of the amount of used resorcin, thereby obtaining a reaction mixture including a 3-(N-monosubstituted amino)phenol, (b) the step of adding an alkyl halide represented by formula (3):

$$R^2X \qquad (3)$$

wherein $R^2$ is the same as defined above; and X is a halogen atom, to the reaction mixture obtained in step (a) to obtain a reaction mixture including the 3-(N,N-disubstituted amino) phenol, (c) the step of adding an aqueous alkaline solution to the reaction mixture obtained in step (b) to dissolve unreacted resorcin in the aqueous alkaline solution, and extracting the 3-(N,N-disubstituted amino)phenol with an organic solvent, and (d) the step of recovering unreacted resorcin from the aqueous alkaline solution layer of step (c).

2. The process for preparing a 3-(N,N-disubstituted amino)phenol according to claim 1 wherein after the reaction is terminated in step (a), the unreacted primary amine is recovered.

3. The process for preparing a 3-(N,N-disubstituted amino)phenol according to claim 1 wherein the conversion of resorcin in step (a) is in the range of 50 to 85 mol %.

4. The process for preparing a 3-(N,N-disubstituted amino)phenol according to claim 1 wherein the reaction in step (a) is carried out in the absence of catalyst.

5. The process for preparing a 3-(N,N-disubstituted amino)phenol according to claim 1 wherein, in step (b), after the alkyl halide is added to the reaction mixture obtained in step (a) to obtain the reaction mixture containing the 3-(N,N-disubstituted amino)phenol, the remaining alkyl halide is removed.

* * * * *

UNITED STATES PATENT AND TRADEMARK OFFICE
CERTIFICATE OF CORRECTION

PATENT NO. : 5,710,335

DATED: : January 20, 1998

INVENTOR(S) : Kenichiro HORIUCHI et al

It is certified that error appears in the above-identified patent and that said Letters Patent is hereby corrected as shown below:

On the title page:, please insert the following references in Section [56]

U.S. Patent Documents:

5,245,081    9/93    Hauptrief et al
5,442,121    8/95    Nagamatsu et al

Foreign Patent Documents:

5-186407    7/93    Japan

Signed and Sealed this

Twenty-third Day of May, 2000

Attest:

Q. TODD DICKINSON

*Attesting Officer*     *Director of Patents and Trademarks*